(12) United States Patent
Glock

(10) Patent No.: US 6,817,239 B2
(45) Date of Patent: Nov. 16, 2004

(54) PIEZOELECTRIC DEVICE

(76) Inventor: Gaston Glock, Klagenfurter Strasse 32a, A-9220 Velden am Woerthersee (AT)

( * ) Notice: Subject to any disclaimer, the term of this patent is extended or adjusted under 35 U.S.C. 154(b) by 0 days.

(21) Appl. No.: 10/263,371

(22) Filed: Oct. 2, 2002

(65) Prior Publication Data

US 2003/0074971 A1 Apr. 24, 2003

(30) Foreign Application Priority Data

Oct. 2, 2001 (DE) .......................................... 101 48 678

(51) Int. Cl.⁷ .............................................. G01L 5/14
(52) U.S. Cl. ........................ 73/167; 310/338; 310/800; 42/1.03; 73/649
(58) Field of Search ..................... 73/632, 649, 12.01, 73/167; 310/338, 334, 800; 42/1.03, 1.02

(56) References Cited

U.S. PATENT DOCUMENTS

| | | | |
|---|---|---|---|
| 5,232,243 A | | 8/1993 | Blackburn et al. |
| 5,838,635 A | * | 11/1998 | Masreliez ................... 367/89 |
| 6,643,968 B2 | * | 11/2003 | Glock ......................... 42/1.02 |
| 2001/0037561 A1 | | 11/2001 | Engbring et al. |

FOREIGN PATENT DOCUMENTS

| | | |
|---|---|---|
| DE | 39 11 804 | 10/1990 |
| DE | 42 12 018 | 10/1992 |
| DE | 199 57 789 | 6/2001 |

* cited by examiner

*Primary Examiner*—John E. Chapman
(74) *Attorney, Agent, or Firm*—Flynn, Thiel, Boutell & Tanis, P.C.

(57) ABSTRACT

A piezoelectric device is assembled from a piezofilm sensor enclosed between two layers of a multilayer board with a printed circuit.

21 Claims, 1 Drawing Sheet

PIEZOELECTRIC DEVICE

FIELD OF THE INVENTION

This invention relates generally to a piezoelectric device.

BACKGROUND OF THE INVENTION

Piezoelectric polymer sensors or piezofilm sensors are increasingly used as piezoelectric sensors. These sensors preferably consist of fluoropolymers, in particular polyvinylidenfluoride (PVDF) and copolymers of PVDF. The piezofilm sensors consist of a piezofilm piece or small plate, on both sides of which is an electrode coating. The electrode coating could be a suitable metal coating, such as silver.

The piezofilm sensor is generally connected to a printed circuit. "Multilayer" circuit boards are preferably utilized for this application because of the high circuit density. However, often there is very little space available for the measuring point, or region, out of the film sensor and the board.

SUMMARY OF THE INVENTION

The purpose of the present invention is to miniaturize a piezoelectric measuring region. According to the device disclosed herein, a piezofilm sensor is enclosed by two adjacent layers of a multilayer circuit board. The piezofilm sensor is thus completely integrated into the circuit board. Therefore, the space occupied by the piezofilm sensor at the measuring region, is reduced. The result is a significant miniaturization of the measuring region. In addition, the piezofilm sensor is protected against mechanical damage by the circuit board.

In order to obtain a large measuring impulse, the piezofilm sensor fills as large a surface as possible between the adjacent layers of the circuit board. The surface of the piezofilm sensor is thus at least one fifth, preferably at least one third, and most preferably more than half the surface of the circuit board. By configuring the piezofilm sensor as a flexible foil, such a large-surface piezofilm sensor easily withstands deformations caused by a mechanical impulse. Preferably, the circuit board and the piezofilm sensor enclosed therein are essentially rectangular in shape. The thickness of the piezofilm sensor is typically less than the thickness of the adjacent layers of the circuit board. Electric connections are provided at the edge of the piezofilm sensor.

It has been determined that forming recesses in the piezofilm sensor does not noticeably influence the sensitivity of the sensor. Accordingly, the piezofilm sensor of the present invention can include recesses to facilitate through-bonding between the layers of the circuit board without impairing the function of the piezofilm sensor. The recesses can be recesses formed along the edge of the essentially rectangular piezofilm sensor or holes formed within the perimeter thereof. To assure greater sensitivity, the piezofilm sensor is preferably positioned in a recess formed in at least one of the two layers of the circuit board between which it is enclosed.

The piezoelectric device of the present invention could be used in many applications as a measuring device wherein mechanical impulses result in a deformation of the piezofilm sensor. These mechanical impulses could result from any suitable source, such as a hit, vibrations or accelerations. The piezofilm sensor could also be configured as a data-receiving mechanism. Thus, the piezofilm sensor could detect if, when and how an article is subjected to movements, hits or other disturbances.

BRIEF DESCRIPTION OF THE DRAWINGS

One embodiment of the device of the present invention and its use in conjunction with a shot counter for pistols will be exemplarily discussed in greater detail hereinafter in connection with the drawings, in which.

DETAILED DESCRIPTION

Figure 1:
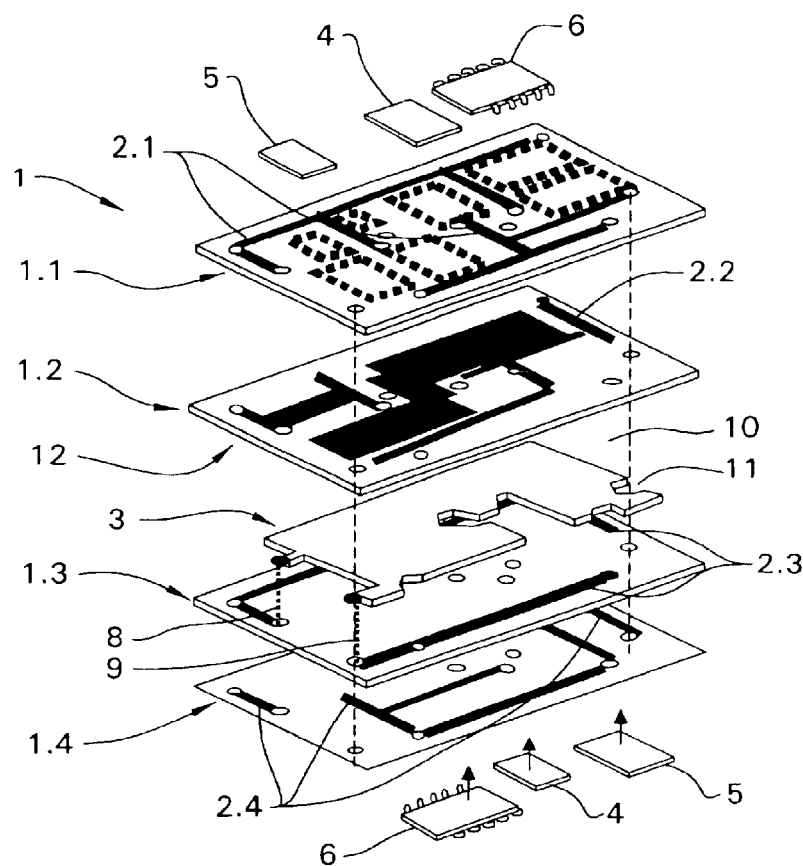
FIG. 1 is an assembly view of a multilayer circuit board including a piezofilm sensor according to the present invention.

Referring to FIG. 1, a rectangular multilayer circuit board 1 includes four layers 1.1, 1.2, 1.3 and 1.4. Each layer 1.1, 1.2, 1.3 and 1.4 includes conductor paths 2.1, 2.2, 2.3 and 2.4, respectively. A piezofilm sensor 3 is enclosed between the inner layers 1.2 and 1.3. The piezofilm sensor 3 has an essentially rectangular shape. The surface of the piezofilm sensor 3 is approximately half the surface of the individual layers 1.1, 1.2, 1.3 and 1.4.

Electronic building components in the form of a capacitor 4, a resistor 5 and an IC chip 6 are connected to the conductor paths 2.1 and 2.4 of the outer layers 1.1 and 1.4. The electrode layers of the piezofilm sensor 3 are connected to the conductor paths 2.3 of the layer 1.3 as illustrated in FIG. 1 by the dashed lines 8 and 9.

To facilitate bonding of the conductor paths 2.1 of the layer 1.1 and the conductor paths 2.4 of layer 1.4 along the dashed line 10, a recess 11 is formed in the piezofilm sensor 3. Additional recesses are also formed along an edge of the piezofilm sensor 3 to allow bonding between the conductor paths 2.1 and 2.2 of the layers 1.1 and 1.2 and the conductor paths 2.3 and 2.4 of the layers 1.3 and 1.4, which are positioned on opposite sides of the piezofilm sensor 3. Furthermore, it is possible to form a recess 12 on the side of the layer 1.2 which faces the piezofilm sensor 3. The recess 12 is sized and configured to receive the piezofilm sensor 3.

Figure 2:
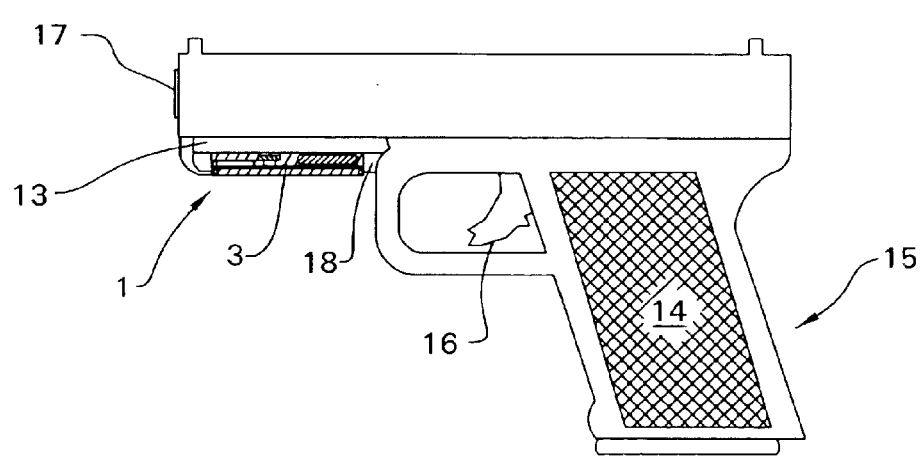
FIG. 2 is a partially sectioned side view of a pistol including an incorporated multilayer circuit board according to FIG. 1, wherein the circuit board is configured as a shot counter.

One use of the present invention is illustrated in FIG. 2. The circuit board 1 is positioned in a recess 18. The recess 18 is formed in a section 13 of the handle 14 of a pistol 15 between the trigger 16 and the barrel muzzle 17. During firing of the pistol 15, the section 13 including the circuit board 1, and thus the piezofilm sensor 3, is deformed by the impulse recoil. This deformation causes the piezofilm sensor 3 to emit a signal to the chip 6 in one of the layers 1.1 or 1.4. The signal is stored as a count impulse in the store of the chip 6. The number of shots fired by the pistol 15 can then be determined with a reading device (not illustrated) configured to read data in the store.

The circuit board 1 with the piezofilm sensor 3 integrated therein can also be inserted into other weapons for the purpose of counting shots fired. For instance, the circuit board 1 could be positioned within the butt plate of a gun or other suitable weapon and operated in a manner similar to that disclosed above.

What is claimed is:

1. A piezoelectric sensor assembly, said assembly comprising:

a first circuit board layer having opposed outer and inner faces;

a second circuit board layer having opposed outer and inner faces, the inner face of the second circuit board layer having an electrode coating applied thereto, wherein the inner face of said first circuit board is disposed toward the inner face of said second circuit board;

a piezofilm disposed between said circuit boards, said piezofilm having first and second opposed faces, wherein the first face of said piezofilm is disposed directly against the inner face of said first circuit board and the second face of said piezofilm is disposed directly against the inner face of said second circuit board, said piezofilm having an outer edge and being shaped to define at least one recess that is located inwardly from adjacent outer sections of said piezofilm; and at least one conductor connecting said circuit board layers extending through the at least one recess defined by said piezofilm.

2. The piezoelectric sensor assembly of claim 1, wherein at least one electrical component is mounted to the outer face of at least one of said circuit board layers.

3. The piezoelectric sensor assembly of claim 2, wherein said at least one electrical component comprises an integrated circuit.

4. The piezoelectric sensor assembly of claim 1, wherein at least one electrical component is mounted to the outer face of each said circuit board layer and said at least one electrical component extends above the outer faces of said circuit board layers.

5. The piezoelectric sensor assembly of claim 1, wherein said circuit board layers comprise a multi-layer circuit board, and wherein the conductor extends through at least one of said board layers to electrically connect said board layers of said multi-layer circuit board.

6. The piezoelectric sensor assembly of claim 1, wherein:
said first and second circuit board layers each subtend an area; and
said piezofilm has an area that is at least one-fifth the area of said circuit board layers.

7. The piezoelectric sensor assembly of claim 1, wherein:
one of said first and second circuit board layers is formed so that the inner face of said one circuit board layer has a recess; and
said piezofilm is seated in the recess of said one circuit board layer.

8. The piezoelectric sensor assembly of claim 1, wherein said piezofilm is configured to generate an electrical signal in response to being exposed to a mechanical impulse.

9. The piezoelectric sensor assembly of claim 1, wherein said piezofilm is configured to generate an electrical signal in response to being exposed to a mechanical impulse from one of the following sources: a hit; vibrations; or an acceleration force.

10. The piezoelectric sensor assembly of claim 1, said piezoelectric sensor assembly being mounted in a weapon for counting a number of discharges of said weapon.

11. A piezoelectric sensor assembly, said assembly including:
a first circuit board layer having opposed outer and inner faces;

a second circuit board layer having opposed outer and inner faces, wherein the inner face of said first circuit board layer is disposed against the inner face of said second circuit board layer;

a piezofilm disposed between said circuit board layers, said piezofilm having an outer edge that defines an outer perimeter of said piezofilm and is further formed so that said outer edge defines at least one recess that is located inwardly from adjacent outer sections of said piezofilm; and at least one electrical conductor that extends between said circuit board layers and through the at least one recess of said piezofilm to electrically connect said circuit board layers together.

12. The piezoelectric sensor assembly of claim 11, wherein at least one electrical component is mounted to the outer face of at least one said circuit board layer.

13. The piezoelectric sensor assembly of claim 12, wherein said at least one electrical component comprises an integrated circuit.

14. The piezoelectric sensor assembly of claim 11, wherein at least one electrical component is mounted to the outer face of each said circuit board layer and said electrical component extends above the outer face of the respective said circuit board layer.

15. The piezoelectric sensor assembly of claim 11, wherein said circuit board layers comprise part of a multi-layer circuit board.

16. The piezoelectric sensor assembly of claim 11, wherein:
said first and second circuit board layers each subtend an area; and
said piezofilm has an area that is at least one-fifth the area of said circuit board layers.

17. The piezoelectric sensor assembly of claim 11, wherein:
one of said first and second circuit board layers is formed so that the inner face of said one circuit board layer has a recess; and
said piezofilm is seated in the recess of said one circuit board layer.

18. The piezoelectric sensor assembly of claim 11, wherein said piezofilm is shaped so that outer portions of the outer edge of said piezofilm generally define a rectangle and said at least one recess is located inwardly of the rectangle defined by the outer portions of the outer edge.

19. The piezoelectric sensor assembly of claim 11, wherein said piezofilm is configured to generate an electrical signal in response to being exposed to a mechanical impulse.

20. The piezoelectric sensor assembly of claim 11, wherein said piezofilm is configured to generate an electrical signal in response to being exposed to a mechanical impulse from one of the following sources: a hit; vibrations; or an acceleration force.

21. The piezoelectric sensor assembly of claim 11, said piezoelectric sensor assembly being mounted in a weapon for counting a number of discharges of said weapon.

* * * * *